United States Patent
Jayan et al.

(10) Patent No.: US 9,974,462 B2
(45) Date of Patent: May 22, 2018

(54) SIGNAL CHARACTERIZATION FOR DETECTING AND/OR ANALYZING DRIVER ACTIVITY

(71) Applicant: CARDIOINSIGHT TECHNOLOGIES, INC., Cleveland, OH (US)

(72) Inventors: Vivek Jayan, Fremont, CA (US); Ping Jia, Solon, OH (US); Ryan Bokan, Lakewood, OH (US); Charulatha Ramanathan, Solon, OH (US); Qingguo Zeng, Solon, OH (US); Torsten Konrad, Heidesheim (DE)

(73) Assignee: Cardioinsight Technologies, Inc., Independence, OH (US)

( * ) Notice: Subject to any disclaimer, the term of this patent is extended or adjusted under 35 U.S.C. 154(b) by 28 days.

(21) Appl. No.: 15/048,835

(22) Filed: Feb. 19, 2016

(65) Prior Publication Data
US 2016/0242663 A1 Aug. 25, 2016

Related U.S. Application Data

(60) Provisional application No. 62/118,344, filed on Feb. 19, 2015.

(51) Int. Cl.
*A61B 5/04* (2006.01)
*A61B 5/046* (2006.01)
(Continued)

(52) U.S. Cl.
CPC ............ *A61B 5/046* (2013.01); *A61B 5/0402* (2013.01); *A61B 5/04012* (2013.01); *A61B 5/18* (2013.01);
(Continued)

(58) Field of Classification Search
CPC ... A61B 5/046; A61B 5/04012; A61B 5/0402; A61B 5/18; A61B 5/4836; A61B 5/0408;
(Continued)

(56) References Cited

U.S. PATENT DOCUMENTS

2004/0176696 A1* 9/2004 Mortara ............... A61B 5/0452
600/515
2006/0281999 A1 12/2006 Li
(Continued)

FOREIGN PATENT DOCUMENTS

EP 0554605 8/1993
WO 02002007 1/2002

OTHER PUBLICATIONS

PCT International Search Report and Written Opinion, Applicant: CardioInsight Technologies, Inc.; International Filing Date: Feb. 19, 2016; Authorized Officer: Yeon Kyung Kim; dated May 26, 2016; 12 pgs.

*Primary Examiner* — Niketa Patel
*Assistant Examiner* — Minh Duc Pham
(74) *Attorney, Agent, or Firm* — Tarolli, Sundheim, Covell & Tummino LLP

(57) ABSTRACT

A system includes an input to receive at least one electrophysiological signal representing cardiac electrical activity measured from a body surface of a patient. The system also includes a signal processor to analyze the at least one electrophysiological signal and compute a score having a value to indicate a likelihood of arrhythmogenic activity, the score being computed as a function of at least two of cycle length, amplitude and polarity of the at least one signal.

19 Claims, 8 Drawing Sheets

(51) Int. Cl.
*A61B 5/0402* (2006.01)
*A61B 5/00* (2006.01)
*A61B 18/12* (2006.01)
*A61B 5/18* (2006.01)
A61B 5/0408 (2006.01)
A61N 1/365 (2006.01)
A61B 18/14 (2006.01)
A61B 18/00 (2006.01)
A61B 18/02 (2006.01)

(52) U.S. Cl.
CPC ........ *A61B 5/4836* (2013.01); *A61B 18/1206* (2013.01); *A61B 5/0408* (2013.01); *A61B 18/1492* (2013.01); *A61B 2018/0072* (2013.01); *A61B 2018/00357* (2013.01); *A61B 2018/00363* (2013.01); *A61B 2018/00577* (2013.01); *A61B 2018/00767* (2013.01); *A61B 2018/00994* (2013.01); *A61B 2018/0212* (2013.01); *A61N 1/365* (2013.01)

(58) Field of Classification Search
CPC ........... A61B 2018/00357; A61B 2018/00363; A61B 2018/00577; A61B 2018/0072; A61B 2018/00767; A61B 2018/00994; A61B 2018/0212
USPC ...................................................... 600/516
See application file for complete search history.

(56) References Cited

U.S. PATENT DOCUMENTS

2013/0251096 A1\* 9/2013 Hiraoka ................. A61B 6/503
378/8
2014/0194763 A1 7/2014 Narayan
2016/0000349 A1\* 1/2016 Sullivan ............. A61B 5/04012
600/509

\* cited by examiner

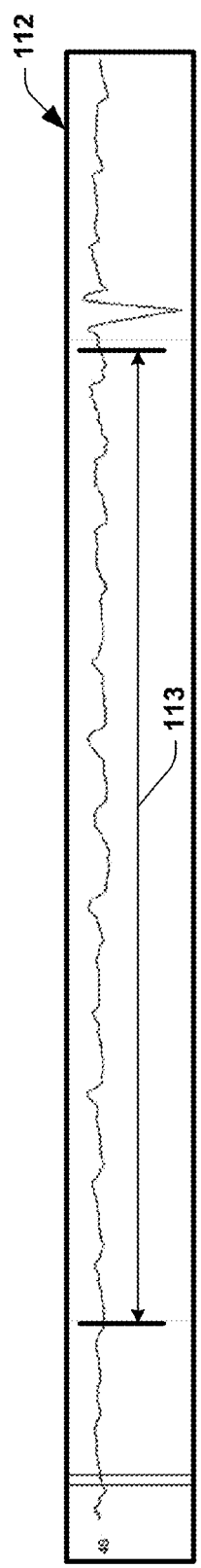
FIG. 9
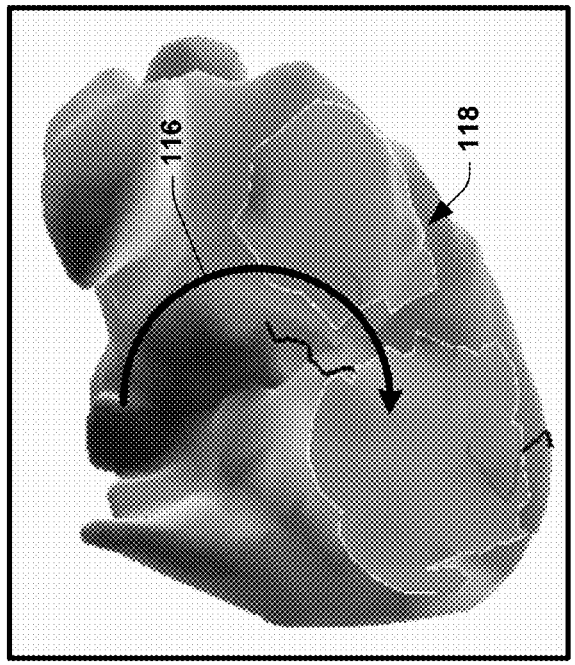
FIG. 10
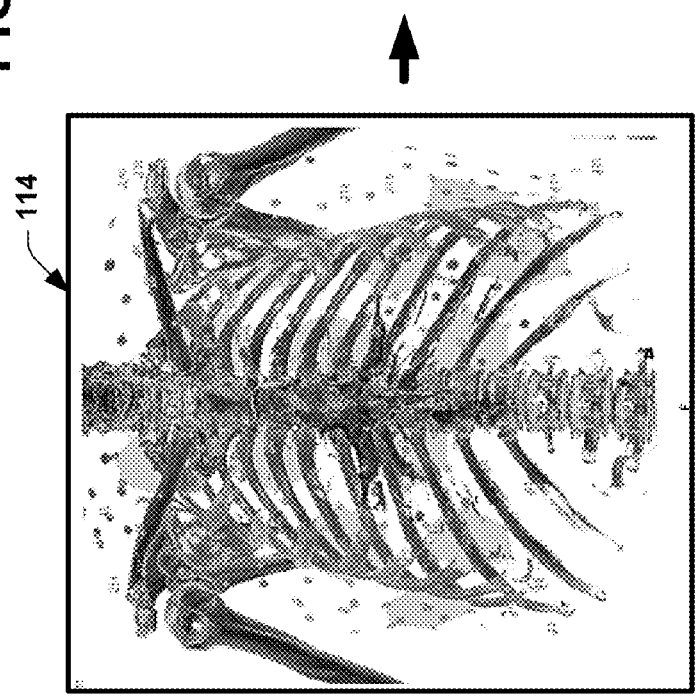

US 9,974,462 B2

SIGNAL CHARACTERIZATION FOR DETECTING AND/OR ANALYZING DRIVER ACTIVITY

CROSS-REFERENCE TO RELATED APPLICATION

This application claims the benefit of U.S. Provisional Patent Application No. 62/118,344, filed 19 Feb. 2015 and entitled SIGNAL CHARACTERIZATION FROM SURFACE ECG, which is incorporated herein by reference in its entirety.

TECHNICAL FIELD

This disclosure relates to characterizing signals for detected and/or analyzing driver activity.

BACKGROUND

Electrocardiography (ECG) is the process of recording the electrical activity of the heart over a period of time using an arrangement of electrodes placed on a patient's body. These electrodes detect electrical changes on the skin that arise from the heart muscle depolarizing during each heartbeat. There are various lead configurations having corresponding electrode placements that can be used to perform electrocardiography (e.g., 12-lead ECG). The waveforms in ECG signals can be printed on paper or visualized on a display for interpretation and analysis.

SUMMARY

This disclosure relates to characterizing signals for detected and/or analyzing driver activity.

As one example, a system includes an input to receive at least one electrophysiological signal representing cardiac electrical activity measured from a body surface of a patient. The system also includes a signal processor to analyze the at least one electrophysiological signal and compute a score having a value to indicate a likelihood of arrhythmogenic activity, the score being computed as a function of at least two of cycle length, amplitude and polarity of the at least one signal.

As another example, one or more non-transitory machine-readable media has data and instructions executable by a processor to perform a method. The data includes measurement data representing at least one electrophysiological cardiac signal measured via at least one electrode positioned a body surface of a patient. The method includes analyzing the measurement data to detect at least one fibrillatory wave interval in at least one electrophysiological signal. The method also includes computing signal characteristics for the at least one fibrillatory wave of each of the at least one electrophysiological signal, the computed signal characteristics including at least two of a change in cycle length for each fibrillatory wave, a change in amplitude of each fibrillatory wave and a polarity change for each fibrillatory wave of the at least one signal. The method also includes indicating a likelihood of stable arrhythmogenic activity based on an evaluation the computed signal characteristics relative to at least one threshold.

BRIEF DESCRIPTION OF THE DRAWINGS

FIG. 9 depicts an example of another electrophysiological waveform.

FIG. 10 depicts an example of a graphical map demonstrating signal characteristics from the signal of FIG. 9.

DETAILED DESCRIPTION

This disclosure relates to characterization of electrophysiological signals for detecting and analyzing arrhythmogenic activity. One or more signals representing cardiac electrical activity can be measured from the body service of a patient, such as from an arrangement of one or more electrodes distributed on the patient's body. Each such signal can be analyzed to characterize certain features of electrical activity that indicates a likelihood of stable driver activity consistent with persistent arrhythmogenic activity, such as fibrillation (e.g., atrial and/or ventricular fibrillation). For example, specific driver sites in the heart are capable of initiation and maintenance of sustained fibrillatory activity. The identification of these driver sites, according to the systems and methods, disclosed herein affords tremendous value in developing and executing patient treatment strategies.

This disclosure provides systems and methods to identify stable arrhythmogenic driver activity solely from signal processing of non-invasive body surface electrical measurements, such as one or more ECG signals. For example, a score can be computed as a function of signal characteristics derived from the measured body surface signal. The signal characteristics include two or more of cycle length, amplitude and polarity of each respective signal. The score and/or its computed constituent signal characteristics can be evaluated relative to one or more corresponding thresholds to ascertain the presence or absence of stable driver activity (e.g., stable rotor and/or focal driver activity). In some examples, the identification of stable arrhythmogenic driver activity can indicate persistent atrial fibrillation (e.g., where arrhythmia is sustained over seven days).

The output results of the signal processing can be presented on a display, such as graphically on a body surface map corresponding to the electrode locations where the one or more signals are measured. In other examples, the resulting signal characteristics can be mapped to a heart model to provide a visualization of the identified arrhythmogenic activity. The output results can provide guidance as a screening tool such as for triaging patients for different possible treatment options. Additionally or alternatively, the output from systems and methods disclosed herein can be used in procedural planning, such as to determine the type of treatment, as well as be utilized intraprocedurally (e.g., providing real time guidance to an endpoint for treatment, such as ablation). As yet another example, systems and methods herein can be utilized as part of post-procedural evaluation.

Figure 1:
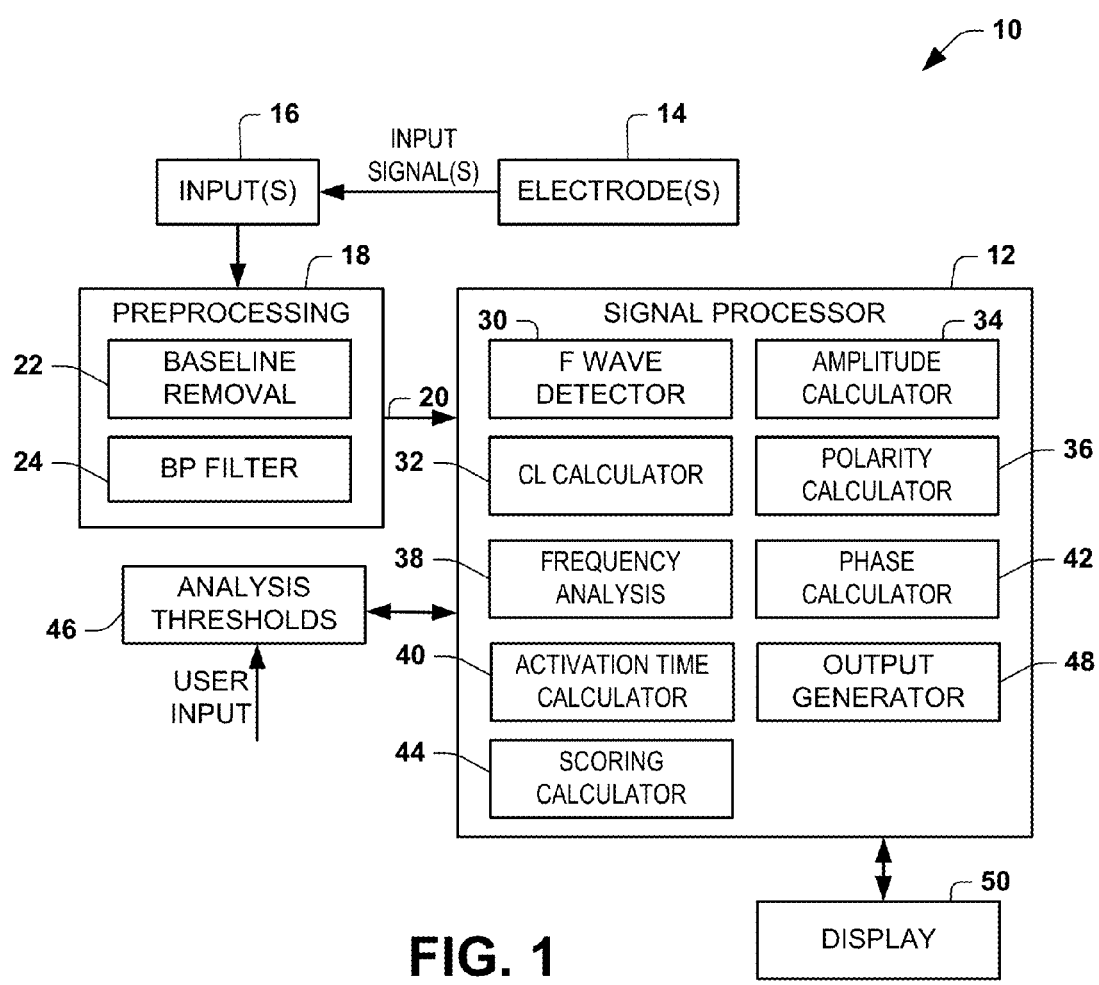
FIG. 1 is an example of a system to characterize signals for detecting/analyzing arrhythmogenic activity.

FIG. 1 is a block diagram illustrating an example of a system 10 that can be implemented to characterize body surface electrical activity for detecting and further analysis of the arrhythmogenic activity. For example, the arrhythmogenic activity can include atrial or ventricular fibrillation corresponding to one or more rotor or focal drivers occurring at a site in the patient's heart. The system 10 can be implemented in a computing apparatus (e.g., including one or more processing cores and storage media) programmed to perform signal processing and analysis on signals received via input interfaces, as disclosed herein.

The system 10 includes a signal processor 12 that includes a set of functions and methods programmed to analyze and characterize one or more body surface electrophysiological signals. For instance, the electrical signals can be measured from one or more electrodes 14, such as can be distributed across a patient's body surface. The one or more electrodes 14 can be a single electrode or a set of electrodes having a prescribed configuration across the patient's thorax. The arrangement of multiple electrodes can include, for example, a 12-lead ECG configuration, a patch containing an arrangement of electrodes distributed thereon or a vest that contains a set of electrodes that can be evenly across a patient's thorax, for example. Regardless of the number and configuration of electrodes, each electrode 14 is positioned to measure body surface electrical activity representing cardiac electrical activity from a body surface of the patient where each electrode has been positioned.

Each of the input signals can be received at a corresponding input interface 16 of the system 10. For example, the electrodes 14 can be connected via corresponding leads that are electrically connected (e.g., via one or more connectors) to the input interface 16. The input interface can include individual input ports or a multi-pin configuration. The input interface can include electrical circuitry (e.g., amplifiers and filter circuits) for each input channel or provide a direct pass through of the received signals. Each channel of the input interface 16 provides a corresponding electrical signal to a preprocessing block 18.

The preprocessing block 18 can include an arrangement of hardware and software to preprocess each received input signal and in turn generate preprocessed electrical physiological signals, demonstrated at 20. In the example system 10, the preprocessing block is configured to remove non arrhythmogenic characteristics from each input signal to provide corresponding preprocessed signal data at 20.

In the example of FIG. 1, the preprocessor 18 is demonstrated as including baseline removal 22 and filtering 24. As one example baseline removal block 22 can be performed by subtracting a mean value of the respective signal. In other examples, the baseline removal 22 can include one or more baseline removal functions, such as high-pass filtering, adaptive filtering, wavelet transform, time frequency analysis, curve fitting or the like. The filter block 24 can be implemented as hardware filter circuit and/or digital filter to remove selected pass bands of frequency content that have been determined to contain non-arrhythmogenic characteristics in their respective signals.

Amplification and additional filtering can also be performed by the preprocessing block 18 to provide the corresponding preprocessed electrical signal data 20. The preprocessed data 20 can be stored in memory (e.g., volatile or non-volatile computer readable media). Thus the preprocessing can also include an analog to digital converter that can be applied to the preprocessing signals to facilitate subsequent processing and analysis by signal processor 12.

The signal processor 12 includes a fibrillatory wave (F wave) detector 30 to identify portions of the processed electrical signals that correspond to fibrillatory waves. For example, the F wave detector 30 can detect the F wave as the portion of each respective electrical signal having a long pause (e.g., greater than a predetermined time interval) between adjacent QRS complexes. For example, QRS signal morphology can be detected within each preprocessed input signal. Additionally, the F wave detector can ascertain the absence of a normal P wave between adjacent QRS complexes, such as by identifying an extended time interval between the adjacent QRS complexes exceeding the predetermined time threshold. In response, to identifying such extended pause between QRS complexes, the F wave detector 30 can classify such portion of the signal as an F wave exhibiting arrhythmogenic activity, such as atrial fibrillation. The F wave detector 30 can identify each F wave automatically or in response to a user input. The F wave detector can tag the input signal data (e.g., with metadata) to specify the start and stop time for each F wave to facilitate further processing.

The signal processor 12 is programmed to analyze the F wave portion of preprocessed input signals. In some examples, where a plurality of input signals are provided from corresponding electrodes, a user interface can be provided (e.g., a graphical user interface (GUI) implemented as part of preprocessing 18) to select which one or more signals to analyze by the signal processor 12. The selection can be made in response to a user input or in an automated manner. The signal processor 12 includes a plurality of calculators to compute various signal characteristics for each F wave identified in one or more input signals. In the example of FIG. 1, the signal processing calculating functions include a cycle length calculator 32, an amplitude calculator 34, a polarity calculator 36, a frequency analysis calculator 38, an activation time calculator 40 and a phase calculator 42. The signal processor thus can employ the various functions 32-42 to compute respective signal characteristics on the F wave portion of the signals and based on the calculated values by such calculators determine a likelihood of stable arrhythmogenic activity, such as stable driver activity consistent with persistent fibrillation.

The cycle length calculator 32 is programmed to compute cycle length for each cycle that occurs during the F wave interval of one or more signals provided in the preprocessed data 20. The cycle length thus corresponds to the interval between start and stop times for each identified cycle that occurs during the F wave. The amplitude calculator 34 is programmed to determine amplitude of the signal during the F wave interval. For example, the amplitude calculator can detect a minimum amplitude and a maximum amplitude of the signal during the F wave and derive an indication of the peak-to-peak amplitude of the signal as the difference between the minimum and maximum amplitudes.

The polarity calculator 36 can determine the polarity of the signal based on the minimum and maximum amplitudes, such as detected by the amplitude calculator 34. The polarity calculator 36 detect whether polarity changes during the F wave interval (e.g., is the signal biphasic during the F wave)

and, if so, the number of times it changes polarity. The frequency analysis calculator 38 analyzes frequency characteristics of each F wave, such as can include frequency spectrum, power of the different frequencies in the respective F wave interval of each respective signal. Additionally or alternatively, the frequency analysis 38 can also identify and determine other frequency characteristics, such as including the dominant frequency as well as harmonics of the signal during detected F wave intervals thereof.

The activation time calculator 40 can also be utilized to ascertain an activation time. The activation time calculator 40 can compute an activation time (or times) for the F wave interval of respective signals. Thus it can be determined if there is sufficient electrical activity for activation (or repolarization) for one or more locations distributed across the body surface during each F wave. One example of activation time of F wave can be calculated based on down-slope zero crossing on filtered ECG data. Another example can be based on minimum dv/dt in a moving window, and yet another example is to use an isophase value (e.g., $\pi/2$) to define activation time of each respective beat. In some examples, the activation time can be used as an approximation to define the start and stop of each individual F wave interval. Activation time can also be applied within the F wave to identify respective cycles used by cycle length calculator 32.

The phase calculator 42 can compute a corresponding phase of each of the one or more signals during the F wave interval thereof. The computed phase thus can be determined over a period of multiple F wave intervals for multiple signals (at multiple body surface locations) and a corresponding indication of spatial and/or temporal phase changes across the body surface can be determined.

The signal processor 12 also includes a scoring function 44 to compute a score that has a value to indicate the likelihood of stable arrhythmogenic driver activity (e.g., an arrhythmogenic stability score). The scoring function 44 can combine two or more of the calculated signal characteristics (e.g., values of which can be stored in memory) to derive the arrhythmogenic stability score. As one example, the scoring function 44 can calculate the arrhythmogenic stability score as a function of the computed cycle length, amplitude and polarity for one or more of the input signals. The scoring function 44 can compute the score based on the raw calculated values, which can be normalized to a respective scale and be aggregated together. The scoring function can apply the normalized aggregate score to a corresponding threshold 46 to determine whether the stable arrhythmogenic driver activity exists or not. In other examples, each of the respective calculators 32-42 can be programmed compare the computed values for each F wave relative to respective analysis threshold 46. The comparisons of the computed values for each calculator relative to its respective threshold thus can be evaluated to ascertain the likelihood of stable arrhythmogenic activity.

The signal processor 12 can also include an output generator 48 to generate an output based on the signal processing. The output generator can provide the output for visualization by a corresponding display device 50. In one example, the output generator 48 provides an indication (e.g., a score) indicating the likelihood of the existence of the arrhythmogenic activity mainly stable driver activity. In another example, such as during intra procedure treatment of the arrhythmogenic activity, the output generator can provide guidance such as in the form of a binary (e.g., yes or no) indication on the display 50. Thus, a healthcare provider can use the output from the signal processor 12 to specify an end point when the treatment can be terminated, such as in response to the output indicating a change to where the stable driver activity is no longer present.

In other examples, the output generator 48 can generate a graphical map of the body surface (e.g., where the one or more electrodes have been positioned) such as to provide a spatial and/or spatial-temporal map of one or more of the computed signal characteristics across the body surface. The signal characteristics can be mapped individually or in combination across the body surface where the electrodes are positioned. As another example, the output generator 48 can map one or more of the computed signal characteristics to a model of a heart, such as to indicate the presence or absence of the stable arrhythmogenic activity in relation to the heart. As disclosed herein, the outputs can be provided in a display to provide guidance as part of the screening process, intraprocedurally during treatment, post-treatment and/or for other types of analysis.

The signal processor 12 can also compute various spatial and/or temporal relationships derived from the computed values (e.g., cycle length, amplitude, polarity, frequency, phase, activation time). For example, the signal processor 12 can be programmed to compute trends in one or more of the computed signal characteristics, such as by analyzing the computed values over a plurality of cycles and over a plurality of F wave intervals for each respective input signal. Changes over time thus can be identified and provided in a corresponding output on the display 50. Additionally or alternatively, spatial variability from one or more of the computed signal characteristics can be analyzed for a plurality of input signals from different body surface locations. For example, when the electrodes are distributed over a portion of the patient's thorax, locations of the electrodes can be known a priori or estimated. Such electrode locations can be relative locations among the different electrodes and/or be relative locations with respect to patient anatomy. In some cases, locations of electrodes can be identified in a graphical user interface (see, e.g., FIG. 13), such as where the electrodes are associated with the vest or a standard 12-lead ECG electrode is utilized. While the locations may or may not be known exactly estimated locations can be utilized to determine spatial variability of one or more of the electrode characteristics that are computed, such as disclosed herein.

Figure 2:
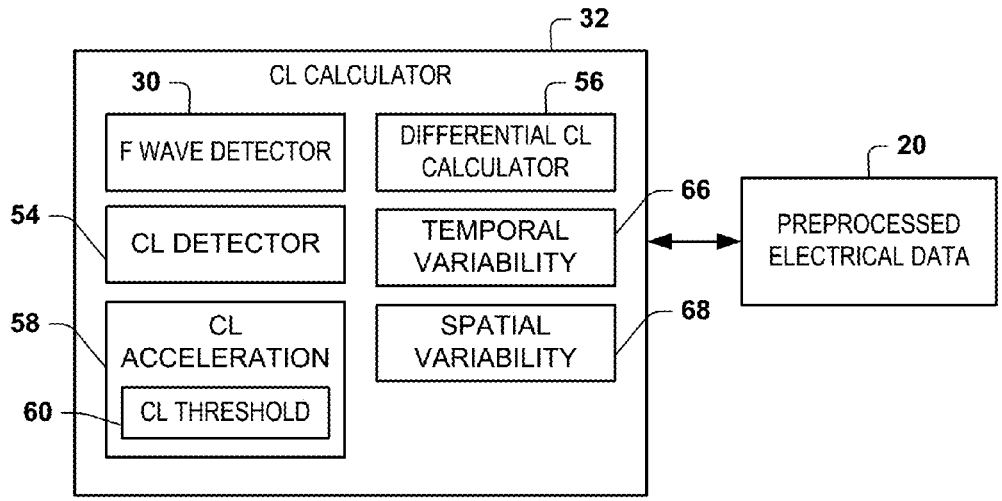
FIG. 2 is an example of a cycle length calculator.

FIG. 2 depicts an example of a cycle length calculator 32. In the example of FIG. 2, the cycle length calculator 32 includes an F wave detector 30 to identify F wave intervals in each of a plurality of input signals as provided in preprocess electrical data 20. While the F wave detector 30 is demonstrated as part of the cycle length calculator 32 in FIG. 2, it is understood that the F wave detector can be applied to the preprocessing electrical data for use by each of the components of the signal processor 12. Thus, the cycle length calculator 32 operates to analyze the F wave intervals of each input signal.

The cycle length calculator 32 includes a cycle length detector 54 to identify and quantify cycle length for the F wave intervals. For example, the cycle length detector 54 can compute the cycle length by employing a dV/dT algorithm applied to compute the time derivative of the electrical potential signals to identify each cycle in each F wave interval. Additionally or alternatively, other signal length detection algorithms could be utilized to identify each cycle, such as including zero crossing or local maximum minimums to identify and quantify each cycle in the F wave interval of each respective signal. A difference between the start and stop times for each cycle thus provides the cycle length thereof, which can be stored in memory.

Based on the cycle lengths determined for each respective signal, cycle length calculator 32 can include differential cycle length calculator 56. Differential cycle length calculator 56 thus can compute cycle length changes between adjacent cycles identified by cycle length detector 54. A cycle length acceleration detector 58 can employ the computed differential of cycle length (e.g., computed by calculator 56) to ascertain whether the cycle length is at a steady state, accelerating or decelerating. For example, acceleration detector 58 can apply a cycle length threshold to the differential cycle length and determine that the cycle length is accelerating (e.g., if it is above the threshold) or decelerating (e.g., if it is below the threshold). Thus, in response to the cycle length calculator 32 detecting that changes between adjacent cycles (e.g., computed by differential cycle length calculator 56) in a given F wave exceed a cycle length threshold 60, the cycle length changes can be stored in memory and utilized by the output generator 48 (along with other computed signal characteristics, such as polarity changes and/or amplitude changes) to indicate a likelihood of stable arrhythmogenic activity.

Figure 3:
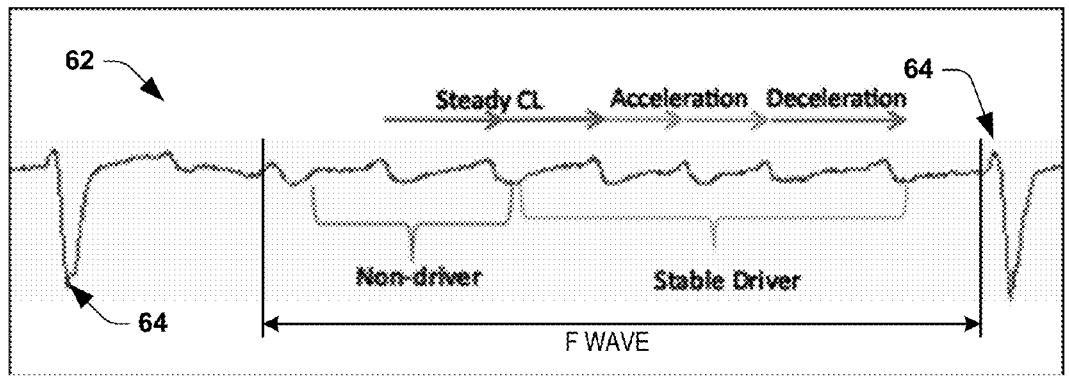
FIG. 3 is an enlarged view of an electrophysiological signal demonstrating characteristics of cycle length, such as can be computed by the cycle length calculator of FIG. 2.

By way of example, FIG. 3 illustrates an example of a signal 62 demonstrating an F wave interval between adjacent QRS complexes 64. In this example, the cycle length calculator 32 applies its methods to ascertain cycle length for each cycle during the F wave interval for the signal 62. The cycle length calculator 32 can also compute differential cycle length over time for the identified cycles. As demonstrated in FIG. 3, a portion of the signal can be identified as a stable driver activity based on identifying that the cycle length changes from a steady value to an acceleration portion and then a decelerating portion over time during the F wave interval.

Referring back to FIG. 2, the cycle length calculator 32 can also include a temporal variability calculator 66 and a spatial variability calculator 68. Temporal variability calculator 66 can evaluate variations in cycle length over time. For example, the temporal variability calculator 66 can compute a variance of cycle length over time for each respective signal, the differential cycle length, such as described above, as well as the standard deviation of the cycle length. The temporal changes of the cycle length for each respective signal provided by the preprocessor electrical data 20 can be performed with respect to a single signal or a plurality of signals acquired from different measurement locations on the body surface.

The spatial variability calculator 68 can be utilized to compute spatial differences in the cycle length across different locations where a plurality of electrode measurements are obtained. In some cases, the electrode measurement locations may be known with respect to patient anatomy, whereas in other examples it is sufficient that signals are measured via electrodes at different locations distributed across the body surface. As an example, the spatial variability calculator 68 can compute a variance of the cycle length across the plurality of electrodes (e.g., electrodes 14) where measurements are obtained. Additionally or alternatively, the spatial variability calculator 68 can compute a differential of the cycle length across different measurement locations and/or a standard deviation of the cycle length across the different measurement locations.

The cycle length calculator 32 can combine outputs from the temporal variability calculator 66 and the spatial variability calculator 68 to compute and monitor trends in the cycle length across the body surface where the electrodes have been positioned for measuring electrophysiological activity for representing the patient's heart. For example, cycle length can be mapped to specific electrode locations such as can be mapped to a graphical model of the patient's torso (see e.g., FIG. 12) or, in some examples to a heart model. By utilizing cycle length threshold 60, the cycle length calculator 32 and/or other methods implemented by the signal processor 12 can identify regions corresponding to fast or slow cycle length or regions where acceleration and/or deceleration may occur in a particular order.

Figure 4:
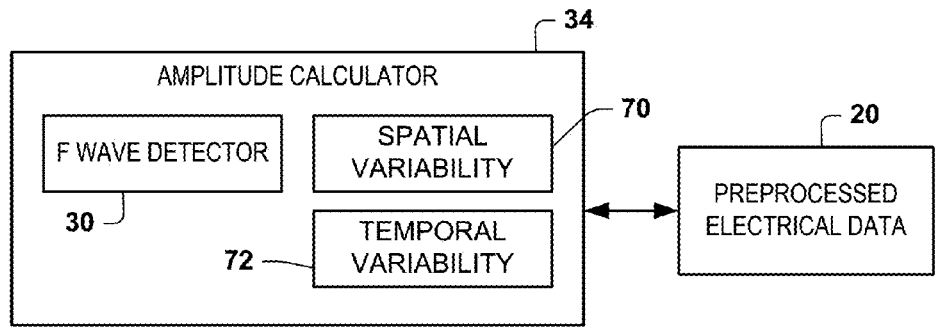
FIG. 4 depicts an example of an amplitude calculator.

As shown in FIG. 4, the amplitude calculator 34 is programmed to compute a measurement of the peak-to-peak electrical signals for each one or more signal that is being analyzed by a signal processor 12. In the example of FIG. 4, the amplitude calculator 34 is applied to the F wave of each input signal. Thus, the amplitude calculator employs the F wave detector 30 to identify the F wave for each respective signal. The amplitude calculator computes a measurement of the minimal amplitude and maximum amplitude of each F wave, such that the computed amplitude represents the peak-to-peak amplitude of the entire F wave. In other examples, peak-to-peak voltages can be ascertained for each cycle within a given F wave.

Amplitude calculator 34 includes a spatial variability calculator 70 to compute spatial variability of the signal amplitude over a plurality of locations where electrode measurements are obtained. The spatial variability calculator 70, for example, can compute the variance of the peak-to-peak voltages for a plurality of measurement locations, a differential of the peak-to-peak voltage between adjacent locations and/or a standard deviation of the peak-to-peak voltages at the different locations.

The amplitude calculator 34 can also include temporal variability calculator 72 to compute and detect temporal availability in the amplitude of the F waves for each input signal provided in preprocessed electrical data 20. For example, the temporal variability calculator 72 can compute a variance in the amplitude, differential of the amplitude between different F waves as well as the standard deviation thereof for each respective input signal. Amplitude calculator 34 thus can compute spatial or temporal availability separately or in other examples can combine spatial and temporal analysis together to ascertain spatial temporal variability, which output generator 48 can utilize to provide a corresponding output thereof.

Figure 5:
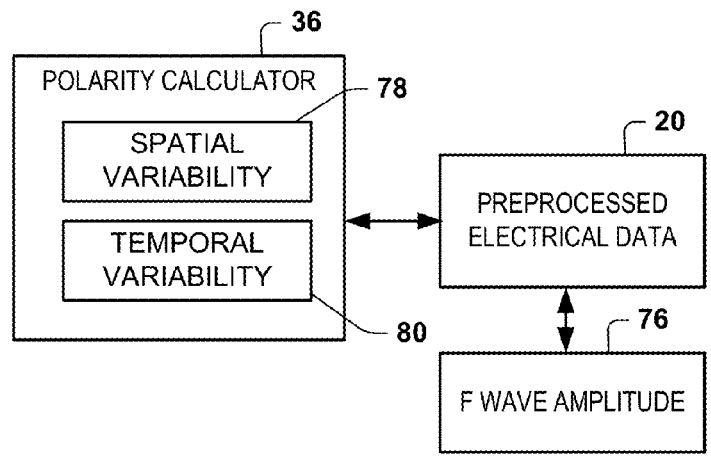
FIG. 5 depicts an example of a polarity calculator.

As shown in FIG. 5, the polarity calculator 36 can compute polarity changes in each F wave for each respective measured signal as provided by the preprocessed electrical data 20. The polarity calculator 36 can ascertain polarity changes based upon the amplitude of each respective F wave determined by the amplitude calculator 34, demonstrated as F wave amplitude data 76. For example, the polarity calculator can determine a change in polarity by determining a zero-crossing or other amplitude change within each F wave interval. The polarity calculator 36 can include spatial variability calculator 78 and a temporal variability calculator 80. The spatial variability calculator 78 can detect spatial variability in the polarity across a plurality of measurement locations. Thus when polarity differences exist or polarity changes occur at different locations such variability the polarity calculator 36 can identify and track the variability. Temporal variability calculator 80 can also detect temporal changes in polarity associated with a corresponding input signal. Thus the temporal changes and polarity can be detected within a signal F wave for a given signal or polarity changes can be identified between sequences of F waves for the signal. The computed polarity and/or variability for each F wave can be stored in memory.

Figure 6:
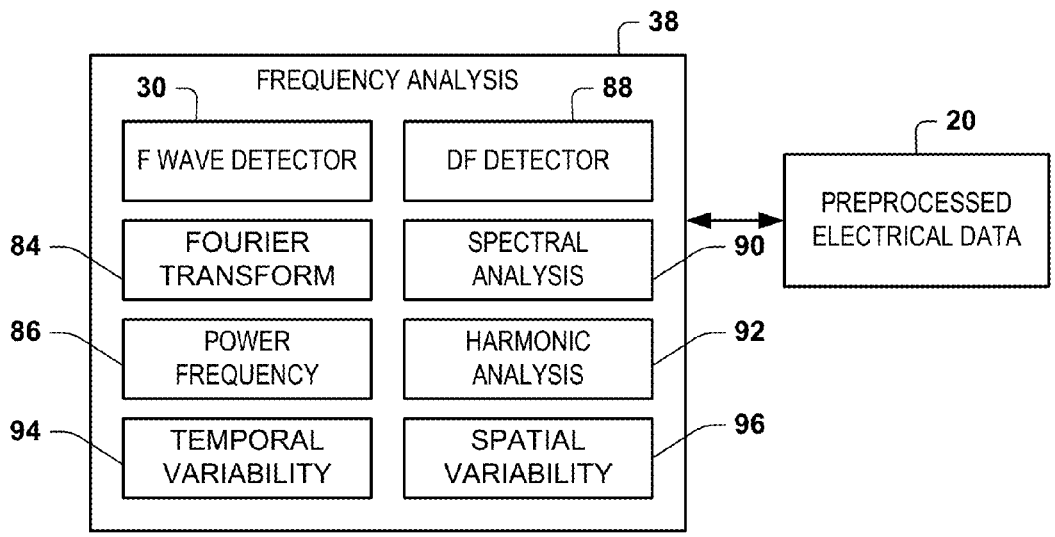
FIG. 6 depicts an example of a frequency analysis calculator.

FIG. 6 depicts an example of the frequency analysis calculator 38. The frequency analysis calculator 38 is programmed to compute frequency characteristics of the input signal provided by the preprocessed electrical data 20. In particular, the frequency analyzer 38 applies its analysis to the F waves of each input signal of the data 20, such as identified by F wave detector 30 for each input signal being processed. In the example of FIG. 6, the frequency analysis calculator 38 includes a Fourier transform to convert the time domain input signal provided by preprocess electrical data into a corresponding frequency domain representation thereof. Thus the Fourier transform 84 can be applied to the F wave windows of each of the signals represented by the electrical data 20. The corresponding frequency domain data can be stored in memory for subsequent processing by a frequency analysis calculator 38.

Additionally, the frequency analysis calculator 38 can include a power frequency detector 86 that determines an indication of power (e.g., absolute or relative power) for each frequency of the signal identified by the Fourier transform component 84. A dominant frequency detector 88 can identify the dominant frequency for each F wave interval such as corresponding to the highest peak and power as determined by the power frequency detector 86. A spectral analysis 90 can also be applied to the frequency domain data for each F wave. For example, the spectral analysis 90 can analyze the distribution of the frequency spectrum such as including the frequency spread and secondary frequency peaks—other than dominant frequency determined by the dominant frequency detector 88. Additional groupings of various frequency components, such as groups of fundamental frequencies, high frequencies and the mean and standard deviations of each of the identified groups of frequencies can also be identified by the spectral analysis 90. The harmonic analysis component 92 can perform analysis of harmonics provided by the frequency spectrum in the frequency data. For example, harmonic analysis component 92 can determine the amplitude of a first harmonic, a second harmonic, and so forth. The harmonic analysis component 92 can also compute gradients between the dominant frequency and the first harmonic.

Similar to other calculators used by signal processor 12, frequency analysis calculator 38 also includes a temporal variability component 94 and a spatial variability calculator 96. The temporal variability calculator 94 can be programmed to compute changes or variations in the frequency characteristics (e.g., as computed by power frequency component 86, dominant frequency detector 88, spectral analysis component 90 and harmonic analysis component 92) for each respective input signal. For instance, the temporal variability can be computed for one or more such frequency characteristics between sequential F waves in each of one or more input signals. Temporal variability thus can include specific statistical information derived from the frequency analysis such as including the variance of the computed frequency characteristics, differential values of such frequency characteristics between adjacent F waves as well as the standard deviation thereof.

Spatial variability calculator 96 can compute spatial variability in the frequency characteristics among different locations across the body surface where each of multiple measurements were made on the body surface. For example, the spatial variability component 96 can determine dispersion and change the frequency characteristics across the body surface. The temporal and spatial variability further may be ascertained and analyzed over time such as in conjunction with treatment to the patient's heart, including drug and/or other delivery of treatment directly to the heart such as via abrasion or the like. The results of the variability can be stored in memory and utilized by output generator 48 to provide a corresponding graphical or other output in the display 50.

Figure 7:
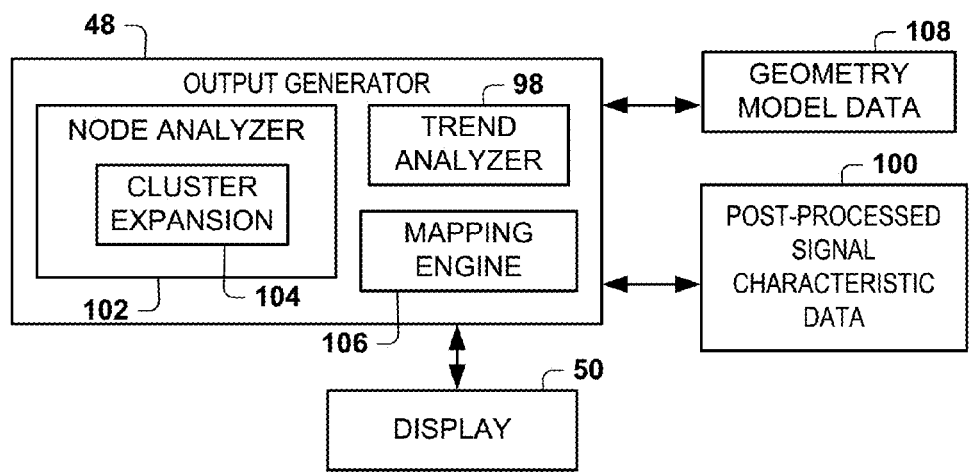
FIG. 7 depicts an example of an output generator and its controls that can be implemented to process signal characteristic data.

FIG. 7 demonstrates output control that can be implemented by the output generator 48 to control the output that is provided based upon the corresponding signal analysis performed by signal processor 12 (e.g., any of computations of FIGS. 1-6). For example, the output generator 48 can include a trend analyzer 98 to analyze post-processed signal characteristic data 100, which can include any of the computed signal characteristics (e.g., computed by one or more of the cycle length calculator 32, amplitude calculator 34, polarity calculator 36, frequency analysis calculator 38, phase calculator 42) over a period of plurality of intervals to identify trends in such data. Additionally, the trend analyzer 98 can analyze the underlying score determined by the scoring calculator 44 that occurs over time based upon the particular analyses that drive the scoring calculator.

The particular calculator signal characteristics that are utilized by the scoring calculator 44 can be selected as a set of default computations. In other examples, the underlying scoring criteria and calculations utilized in computing the score can be selected in response to a user input. Additionally, associated thresholds 46 for each of the computations and scores can be set according to the patient and/or in response to user inputs. The trend analyzer 98 can identify trends in the data that change over time. For example, the trends can be based upon monitoring the data where no treatment is being delivered (e.g., pre-treatment during screening or post-treatment). In other examples, the trend analyzer 98 can monitor changes in the computed electrical signal characteristics to detect trends in signal characteristics that might occur over time in response to application of therapy to the patient's heart. For example, the therapy can include chemical therapy, or electrical therapy (i.e., such as ablation, pacing or the like).

A mapping engine 106 can receive the trend data determined by the trend analyzer 98 or any computations of the signal processor 12 and generate a corresponding output thereof on the display 50. For example, the mapping engine 106 can employ geometry/model data 108 into which the resulting trends can be graphically represented in the display 50. The geometry/model data 108, for example, can include data representing the body surface, such as a two-dimensional or three-dimensional model representation of the body surface where the electrical measurements are obtained (e.g., by electrodes 14).

As mentioned, in some examples, the location of electrodes on the body surface may be defined by the geometry data 108 such that the electrode locations are known with respect to patient's geometry. The electrode locations may be determined with respect to patient's geometry based upon image data that is obtained while the electrodes are attached to the patient's body. In other examples, the location of the electrodes may not be known with respect to the patient's anatomy by imagining data. In such other examples, the location of the electrode measurement locations can be estimated based upon the locations where such electrodes are typically positioned (e.g., 12 lead ECG electrode locations). As yet another example, the electrode locations may be determined as relative locations among electrodes in which the positions of electrodes may be known in 2D or 3D space further relative to other electrodes apart from any patient geometry information (e.g., in the absence of geometry information derived from imaging).

The output generator 48 can also include a node analyzer 102 to determine spatially significant trends based upon the trend analysis data by trend analyzer 98 or other post processed signal characteristic data 100. For example, the electrical characteristics that are computed at one electrode node can be expanded from that electrode to a cluster of one or more neighboring electrodes. The expansion from a given electrode node can be controlled by cluster expansion component 104. The cluster expansion component 104 can evaluate the computed electrode characteristics of each node relative to its neighbors and expand out to include additional neighboring electrodes in a cluster until the observed trend (by trend analyzer 98) does not match.

For example, cluster expansion component 104 can correlate one or more computed electrical characteristics (e.g., provided by signal characteristic data 100) for a group of contiguous nodes, with respect to a starting node, and compare the characteristics for each neighboring node relative to a corresponding threshold to identify stable arrhythmogenic activity. In response to determining that the correlation between nodes and the corresponding thresholds no longer matches the starting node, expansion can be terminated and the cluster of nodes can thus be identified as the set of nodes that matched the common criteria of the starting node. For example, the analysis and expansion can be repeated over an expanding set of nodes to obtain a cluster of contiguous neighboring electrodes that each includes a common set of signal characteristics identifying stable driver activity. As disclosed herein, for example, the stable driver activity for each respective node can be based upon computing a score relative to one or more thresholds that specify stable rotor activity.

The node analyzer 102 and cluster expansion 104 can be utilized to identify a plurality of clusters over time, which clusters can be graphically represented by the mapping engine 106 with respect to the geometry model data. For example, the mapping engine 106 can display each cluster and/or nodes in each cluster in a color coded scale, which color scale indicates the number of times of each electrode node in the cluster has met the clustering criteria. The mapping engine can display the color-coded graphical map displayed on a corresponding model of the body surface. In other examples, the clustering data can be displayed on a model of a heart, such as according to the geometry model data 108.

As a further example, for the example of cases involving multi-electrodes, an indication of the arrhythmogenicity of the heart can be determined by monitoring the Body surface signal for driver activity in the following way:
a) Identify ECG segments where there is acceleration and deceleration of CL, a Frequency shift, a trend of amplitude increasing or decreasing, or polarity change. Cutoff threshold for these markers can be defined per patient, and can be derived from CL variance or amplitude variance (e.g., determined by cycle length calculator 32).
b) Cluster expansion 104 can expand from that single electrode to a cluster of neighboring electrodes until the trend observed in (a) does not match based on correlation and an adjustable threshold.
c) This cluster is now indicated as housing driver activity.
d) The functions of (a) to (c) can be repeated over time to identify multiple clusters, which output generator can display on a graphical map of the body surface and/or plot to a model of the heart.
e) Each electrode node will have a running count of how many times it has been implicated as part of a cluster, and this count can be indicated in a graphical map according to a color scale value.

The output map thus provide a measure of arrhythmogenic tissue, such as follows:
 i. The more a node is implicated, the more it would be considered a region of highly arrhythmogenic tissue.
 ii. The more areas that are implicated would indicate a more arrhythmogenic heart.

The effect of ablation, drug administration, tissue remodeling can be addressed by utilizing a sliding window of time (e.g., user defined window). The measure of arrhythmogenicity can be updated during the recording period As a further example, example configurations involving any number of electrodes (e.g., a single electrode, or a standard 12 lead ECG), the arrhythmogenicity of the heart can be measured by monitoring the body surface signal for stable driver activity as follows:
a) Identify ECG segments where there is acceleration or deceleration, a Frequency shift, a trend of amplitude increasing or decreasing, or polarity change. Cutoff threshold for these markers can be defined per patient, and can be derived from CL variance or amplitude variance.
b) In other examples, the number of segments containing a given trend can be tracked and the cumulative time of these segments be divided by the total recording time.

For instance, the node analyzer 102 can maintain a running count of the number of times that the signal for each electrode node has met the clustering criteria as to indicate an F wave at such measurement location that has been determined to correspond to stable driver activity. The count for each node thus increments in proportion to the number of times its signal manifests stable driver activity. A color or other scale is applied to the count value which the mapping engine 106 can apply to visualize graphically the indication of each node within a given cluster and the graphical model. Thus a corresponding indication of stable arrhythmogenic activity can be provided in the graphical output. For example, the more a given node is implicated to indicate a stable driver activity, such as based on the computed score exceeding a threshold, the greater likelihood that one or more regions of the heart contains arrhythmogenic tissue exhibiting persistent fibrillation. Additionally a greater number of regions across the surface that are implicated to meet the criteria will indicate a greater amount of arrhythmogenic tissue in the patient's heart.

The output generator 48 can display the result to indicate a percentage of time the patient exhibited arrhythmogenic driver trends. This percentage can provide a measure or arrhythmogenicity without mapping to a body surface. In other examples, the results can be mapped to provide a corresponding visualization. Similar analysis and graphical output can be displayed intraprocedurally, such as during a treatment procedure, as disclosed with respect to pre- and post-treatment. For example, the effect of treatment, such as ablation (e.g., RF, cryogenic, etc.), chemical administration, tissue remodeling can be demonstrated over time during such treatment by observing corresponding decreases in the amount of arrhythmogenic activity for the various nodes in the graphical output of the patient's heart.

Figure 8:
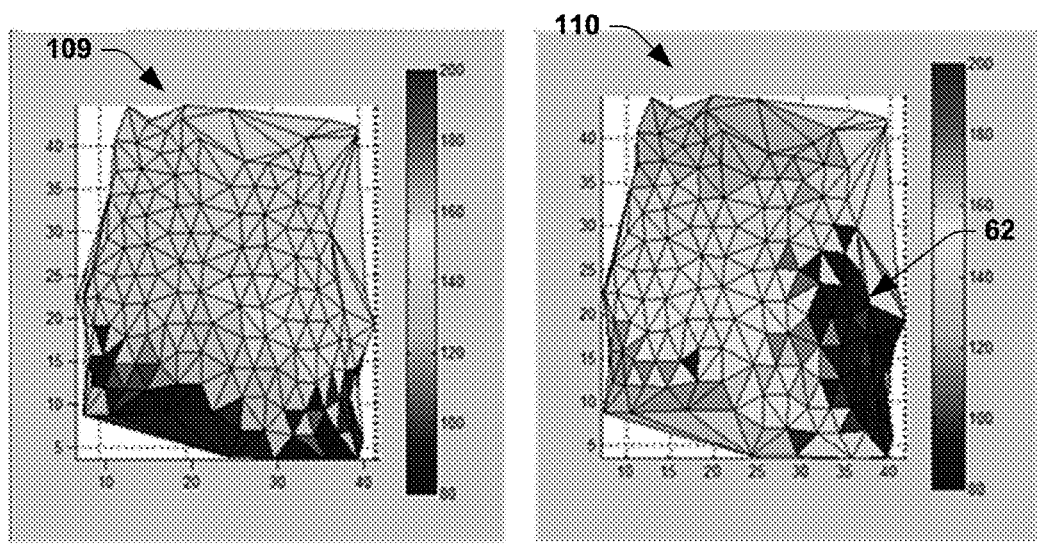
FIG. 8 depicts examples of spatial cycle length dispersion derived from signals acquired across a patient's thorax.

As a further example, FIG. 8 demonstrates two example graphical output maps 109 and 110 that the mapping engine 106 can generate across the body surface of a patient according to measurements at a plurality of electrodes. Each of the graphical maps 109 and 110 demonstrates changes in arrhythmogenic activity that have been identified and detected by the node analyzer 102. In the example of FIG. 8, the map 109 demonstrates spatial cycle length dispersion recorded from a multi-electrode ECG for a non-driver F wave window and map 110 demonstrates detected stable driver for another F wave window. In this example, the respective graphical maps 109 and 110 occurred sequentially, such that a spatial temporal analysis (e.g., by CL calculator 32 employing temporal and spatial variability calculators 66 and 68) could be employed to identify such driver mechanisms. An area of fast cycle length activity can also be identified, such as demonstrated at 111 as cluster of darker nodes, which would be evident to a physician. While the example of FIG. 8 demonstrates cycle length dispersion, other signal characteristics and changes thereof could be mapped and plotted in a similar manner individually or in combination with any other signals and characteristics disclosed herein.

By way of further example, FIG. 9 depicts an example of a signal 112 that includes an F wave 113 (e.g., identified by F wave detector 30). The signal 112, for example can correspond to any one of the electrodes that have been distributed across the patient's heart such as demonstrated in the electrode distribution shown at 114 in FIG. 10. In the example of FIG. 10, the electrode distribution at 114 is shown with respect to the patient's anatomy, such as can be obtained by identification and registration of electrode locations in geometry data derived from an imaging modality (e.g., CT scan, MRI or the like). The F wave 113 of the signal 112 can be analyzed by signal processor 12 and its various components, such as disclosed herein, to determine whether or not there is stable arrhythmogenic driver activity in the F wave. In the example of FIG. 10, the signal processing of F wave (e.g., by signal processor 12) is shown to identify stable rotor activity in the left atrium as demonstrated at arrow 116 superimposed on a model of the heart 118. As an example, the rotor activity 116 can be confirmed by other methods, such as by solving the inverse problem with respect to sensor data distributed across the patient's heart and reconstructing the electrograms onto the heart model 118.

Figure 11:
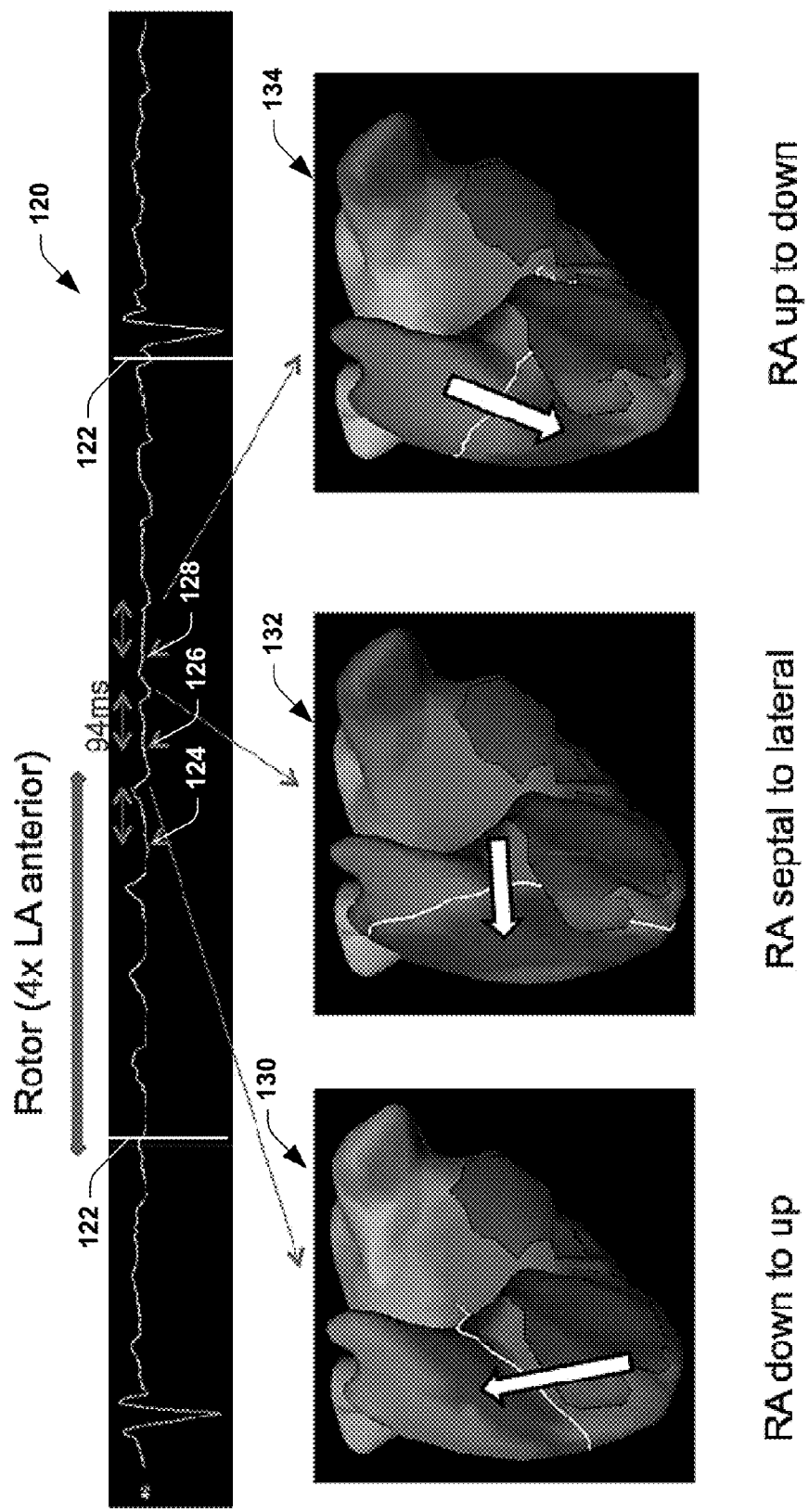
FIG. 11 depicts examples of a waveform and graphical maps demonstrating mapping of the electrophysiological signal to propagation of electrical signals across a model of the heart.

FIG. 11 demonstrates another example of how stable rotor activity detected by signal processor 12 can correspond to stable rotor activity of a patient's heart. In FIG. 11, a non-invasively sensed signal 120 (e.g., preprocessed electrical signal 20) is demonstrated that includes a detected F wave between timing calipers 122. The F wave contains a plurality of cycles 124, 126 and 128. Each of the cycles is indicative of a corresponding heart of stable rotor activity and thus can map to a corresponding region of the heart, such as demonstrated in models 130, 132 and 134. For example, the cycle 124 can correspond to down-to-up stable rotor motion in the right atrium. For example, in the model 130, the detected cycle 124 can correspond to stable rotor motion that is in the right atrium from down to up. The cycle 126 can correspond to septal to lateral rotor motion in the right atrium and the cycle 128 of the F wave can correspond up-to-down movement of the rotor in the right atrium as demonstrated in model 134.

Figure 12:
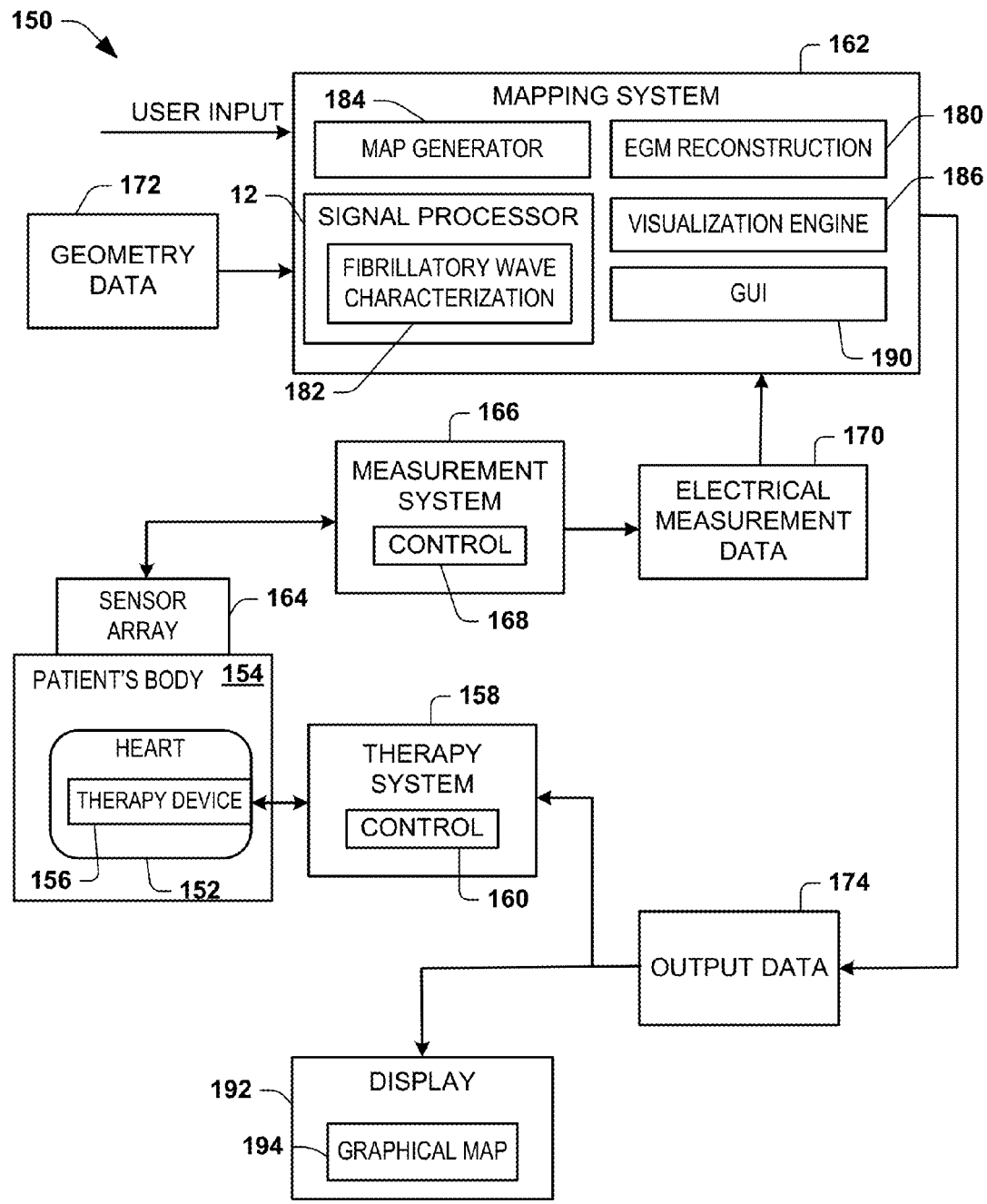
FIG. 12 depicts an example of a system to implement fibrillatory wave characterization.

FIG. 12 depicts an example of a system 150 that can be utilized for generating an output to process body surface signals to characterize arrhythmogenic activity of a patient, including helping diagnose stable fibrillatory drive activity. In some examples, the system 150 can generate a graphical map (e.g., a body surface map or a map on a heart model) 194 and/or display processed electrical signals. The system can also provide information in other formats to provide guidance to the user indicative of one or more of computed signal characteristics as well as information derived from such computed signal characteristics.

As disclosed herein, the system 150 has applications throughout various phases of patient care. As an example, the system can be used as part of a patient screening process (e.g., as part of a diagnostic and/or treatment planning procedure or to perform post-treatment evaluation. Additionally, the system 150 can be utilized as part of a treatment procedure, such as to determine parameters for delivering a therapy to the patient (e.g., delivery location, amount and type of therapy). For example, a catheter, having one or more therapy delivery devices 156 affixed thereto can be inserted into the body 154 as to contact the patient's heart 152, endocardially or epicardially. Those skilled in the art will understand and appreciate various type and configurations of therapy delivery devices 156 that can be utilized, which can vary depending on the type of treatment and the procedure. For instance, the therapy device 156 can be configured to deliver electrical therapy, chemical therapy, sound wave therapy, thermal therapy or any combination thereof.

By way of further example, the therapy delivery device 156 can include one or more electrodes located at a tip of an ablation catheter configured to generate heat for ablating tissue in response to electrical signals (e.g., radiofrequency energy) supplied by a therapy system 158. In other examples, the therapy delivery device 156 can be configured to deliver cooling to perform ablation (e.g., cryogenic ablation), to deliver chemicals (e.g., drugs), ultrasound ablation, high-frequency radio frequency ablation, or a combination thereof. In still other examples, the therapy delivery device 156 can include one or more electrodes located at a tip of a pacing catheter to deliver electrical stimulation, such as for pacing the heart, in response to electrical signals (e.g., pacing current pulses) supplied by a therapy system 158. Other types of therapy can also be delivered via the therapy system 158 and the invasive therapy delivery device 156 that is positioned within the body.

As a further example, the therapy system 158 can be located external to the patient's body 154 and be configured to control therapy that is being delivered by the device 156. For instance, the therapy system 158 includes controls (e.g., hardware and/or software) 160 that can communicate (e.g., supply) electrical signals via a conductive link electrically connected between the delivery device (e.g., one or more electrodes) 156 and the therapy system 158. The control system 160 can control parameters of the signals supplied to the device 156 (e.g., current, voltage, repetition rate, trigger delay, sensing trigger amplitude) for delivering therapy (e.g., ablation or stimulation) via the electrode(s) 154 to one or more location of the heart 152. The control circuitry 160 can set the therapy parameters and apply stimulation based on automatic, manual (e.g., user input) or a combination of automatic and manual (e.g., semiautomatic controls). One or more sensors (not shown) can also communicate sensor information back to the therapy system 158. The position of the device 156 relative to the heart 152 can be determined and tracked intraoperatively via an imaging modality (e.g., fluoroscopy, xray), a mapping system 162, direct vision or the like. The location of the device 156 and the therapy parameters thus can be combined to determine corresponding therapy delivery parameter.

Before, during and/or after providing a therapy via the therapy system 158, another system or subsystem can be utilized to acquire electrophysiology information for the patient. In the example of FIG. 12, a sensor array 164 includes one or more body surface electrodes that can be utilized for measuring patient electrical activity. As one example, the sensor array 164 can correspond to a high-density arrangement of body surface sensors (e.g., greater than approximately 200 electrodes) that are distributed over a portion of the patient's torso (e.g., thorax) for measuring electrical activity associated with the patient's heart (e.g., as part of an electrocardiographic mapping procedure). An example of a high-density body surface non-invasive apparatus that can be used as the sensor array 164 is shown and described in International Application No. PCT/US2009/063803, filed 10 Nov. 2009. Other arrangements and numbers of sensing electrodes can be used as the sensor array 164. For example, the array can be a reduced set of electrodes, which does not cover the patient's entire torso and is designed for measuring electrical activity for a particular purpose (e.g., an array of electrodes specially designed for analyzing AF and/or VF) and/or for monitoring a predetermined spatial region of the heart. In other examples, an array having a traditional or modified 12-lead ECG or a single electrode can be implemented as the sensor array 164 to provide body surface electrical signals.

One or more sensors may also be located on the device 156 that is inserted into the patient's body. Such sensors can be utilized separately or in conjunction with the non-invasive sensor array 164 for mapping electrical activity for an endocardial surface, such as the wall of a heart chamber, as well as for an epicardial surface. Additionally, such electrode can also be utilized to help localize the device 156 within the heart 152, which can be registered into an image or map that is generated by the system 150. Alternatively, such localization can be implemented in the absence of emitting a signal from an electrode within or on the heart 152.

In each of such example approaches for acquiring patient electrical information, including invasively, non-invasively, or a combination of invasive and non-invasive sensing, the sensor array(s) 164 provide the sensed electrical information to a corresponding measurement system 166. The measurement system 166 can include appropriate controls and signal processing circuitry (e.g., corresponding to preprocessing block 18 of FIG. 1) 168 for providing electrical measurement data 170 that describes electrical activity detected by the sensors in the sensor array 164. For example, Signal processing circuitry of the measurement system 166 can convert the signal(s) to corresponding digital information. The measurement system can further process the digital information corresponding to one or more electrophysiological signals from sensor array 164 and remove non-arrhythmogenic characteristics from each such signal and to provide preprocessed data that is stored in memory as the electrical measurement data 170.

The control 168 can also be configured to control the data acquisition process for measuring electrical activity and providing the measurement data 170. In some examples, the control 168 can control acquisition of measurement data 170 separately from operation of the therapy system 158, such as in response to a user input. In other examples, the measurement data 170 can be acquired concurrently with and in synchronization with delivering therapy by the therapy system, such as to detect electrical activity of the heart 152 that occurs in response to applying a given therapy (e.g., according to therapy parameters). For instance, appropriate time stamps can be utilized for indexing the temporal relationship between the respective measurement data 170 and therapy parameters use to deliver therapy as to facilitate the evaluation and analysis thereof.

The mapping system 162 is programmed to combine the measurement data 170 corresponding to sensed body surface electrical activity of the heart 152 to provide corresponding output data 174. The output data 174 can be represent or characterize arrhythmogenic activity of the heart, such as to identify the presence or absence of stable fibrillatory driver activity (e.g., rotor and/or focal drivers).

As one example, the output data 174 can include one or more maps derived from the electrical measurement data acquired for the patient over one or more time intervals (e.g., before, after or during a study or treatment procedure). In an example where the sensor array 164 includes a plurality of electrodes, the output data 174 can include one or more output graphical maps for the patient's body surface (see, e.g., FIG. 8). In other example, the computed data can be mapped to a geometric surface of a heart model. As disclosed herein, the maps can be computed based on electrical data that is acquired non-invasively via one or more electrodes in the sensor array 164 distributed on the surface of the patient's body 154.

Since the measurement system 166 can measure electrical activity of a predetermined region or the entire heart concurrently (e.g., where the sensor array 164 including a plurality of electrodes covering the entire thorax of the patient's body 154), the resulting output data (e.g., phase characterizations and/or other electrocardiographic maps) thus can also represent concurrent data for the predetermined region or the entire heart in a temporally and spatially consistent manner. The time interval for which the output data/maps are computed can be selected based on user input. Additionally or alternatively, the selected intervals can be synchronized with the application of therapy by the therapy system 158. As disclosed herein, the indication of the presence or absence of stable arrhythmogenic activity can be computed from the body surface electrical signal(s) in the absence of performing electrogram reconstruction based on patient geometry.

In other examples, where additional information may be available and geometry data 172 can be obtained, the system may include electrogram reconstruction 180 programmed to compute an inverse solution and provide corresponding reconstructed electrograms based on the process signals and the geometry data 172. For example, the geometry data 172 can correspond to a mathematical model, such as can be a generic model or a model that has been constructed based on image data obtained for the patient (e.g., via an imaging modality, such as CT, MRI, bi-plane xray or the like) and provides spatial coordinates for the patient's heart 152 and electrodes on the sensor array. The reconstructed electrograms thus can correspond to electrocardiographic activity across a cardiac envelope, and can include static (three-dimensional at a given instant in time) and/or be dynamic (e.g., four-dimensional map that varies over time). Examples of inverse algorithms that can be utilized in the system 10 include those disclosed in U.S. Pat. Nos. 7,983,743 and 6,772,004. The EGM reconstruction 180 thus can reconstruct the body surface electrical activity measured via the sensor array 164 onto a multitude of locations on a cardiac envelope (e.g., greater than 1000 locations, such as about 2000 locations or more). In other examples, the mapping system 162 can compute electrical activity over a sub-region of the heart based on electrical activity measured invasively, such as via a basket catheter or other form of measurement probe (e.g., on or attached to device 156).

The mapping system 162 include a signal processor 12 that implements fibrillatory wave characterization 182, which can be implemented according to any of the example methods and calculators of the signal processor disclosed herein, individually and/or in combination (see, e.g., FIGS. 1-6 and associated description). For example, the fibrillatory wave characterization 182 can detect wave intervals in each signal provided in the electrical measurement data 170. The signal processor can apply the fibrillatory wave characterization 182 to the F wave intervals to compute desired signal characteristics of the F wave windows, which can include two or more of cycle length, amplitude and polarity of each signal being processed. Other calculators can also be implemented by the fibrillatory wave characterization 182 of signal processor 12. Signal processor thus can apply a predetermined threshold to each computed signal characteristic or a combined score derived from the computed characteristics to provide corresponding output data 174 that indicates the presence or absence of stable arrhythmogenic driver activity (e.g., stable rotor and/or focal driver activity). In some examples, the identification of stable arrhythmogenic driver activity can specify the presence of persistent atrial fibrillation, such as based on comparing a computed score (derived from computed signal characteristics) relative to one or more predetermined thresholds that specify stable rotor activity.

By way of example, if the signal processor 12 determines that the differential cycle length for a given F wave for one or more electrodes exceeds a time threshold (e.g., about 10 ms) and determines the presence of one or both (i) polarity changes and/or (ii) amplitude changes exceeding a voltage threshold (e.g., about 0.05 mV) in the given F wave, the signal processor can aggregate such information to provide a score to identify the presence of stable driver activity in the patient's heart. If the score does not rise above the threshold, for example, the signal processor can determine a high likelihood of the absence of stable driver activity.

In addition to general screening from body surface electrical measurements to determine that the patient's heart exhibits stable driver activity, geometry data 172 can be used to specify a geometrical correspondence between a given electrode or set of electrodes and a region of the heart. For example, by acquiring geometry data for a given patient while wearing the sensor array 164, the geometry data can be utilized to identify a zone of one or more electrodes in the sensor array that map deterministically to a given region of the heart 152. Alternatively, a generic model (e.g., describing geometric relationship between a generic heart and body surface) may also be utilized to specify a geometrical correspondence between a one or more electrodes and a region of the heart. Regardless of how the geometrical correspondence is determined (e.g., via patient imaging, a priori information, or a model), electrical activity measured by the given zone on the body surface can provide a rough estimate of electrical activity for the given region of the heart. As a result, a health care provider can monitor the electrical activity and signal characteristics computed by the signal processor 12 to ascertain the impact of treatment applied to the heart. This can be part of the treatment process to help guide the process to a desired end point where the stable driver activity has been removed.

Additionally, the mapping system 162 can compute an indication of arrhythmogenic activity (e.g., driver activity, such as rotors and focal) based on the reconstructed electrical activity. As mentioned, the reconstructed electrical activity can be computed to a cardiac envelope by solving the inverse problem based on measured body surface electrical activity (e.g., electrograms) and the geometry data 172. The driver activity on the cardiac envelope can be used to confirm the detected stable driver activity that is determined by the signal processor 12 based on analysis only of one or more body surface signals (without geometry data). Additionally or alternatively, the driver activity on the cardiac envelope can be used to more particularly identify one or more spatial locations on the heart associated with the driver activity. The spatial locations on the heart thus can be used to identify one or more treatment sites for positioning the therapy device to deliver treatment to the patient's heart 152. An example of how the reconstructed electrical information An output generator 188 can be programmed to generate one or more maps based on the computed electrical information provided in the output data 174. For example, the map generator 162 can provide the output data with an indication or characterization of monitored signals (e.g., a measure specifying an amount of arrhythmogenicity for the heart) determined by the function 182. The output data 174 can be converted to a graphical representation for display by a visualization engine 186. Parameters associated with the graphical representation, corresponding to an output visualization of the computed map, such as including selecting a time interval, a type of information that is to be presented in the visualization and the like can be selected in response to a user input via a corresponding visualization GUI 190. The mapping system 162 includes visualization engine 186 that provides the output data 174 in desired video format that can in turn be visualized on the display 192, including graphical map 194 as well as other visual outputs disclosed herein.

Additionally, the output data 174 can be utilized by the therapy system 158. The control that is implemented can be fully automated control, semi-automated control (partially automated and responsive to a user input) or manual control based on the output data 174. In some examples, the control 160 of the therapy system can utilize the output data to control one or more therapy parameters. As an example, the control 160 can control delivery of ablation therapy to a site of the heart (e.g., epicardial or endocardial wall) based on arrhythmogenicity that has been determined by the function 182. For instance, the delivery of therapy can be terminated automatically in response to detecting the absence of stable driver activity. In other examples, an individual can view the map generated in the display to manually control the therapy system based on information that is visualized. Other types of therapy and devices can also be controlled based on the output data.

Figure 13:
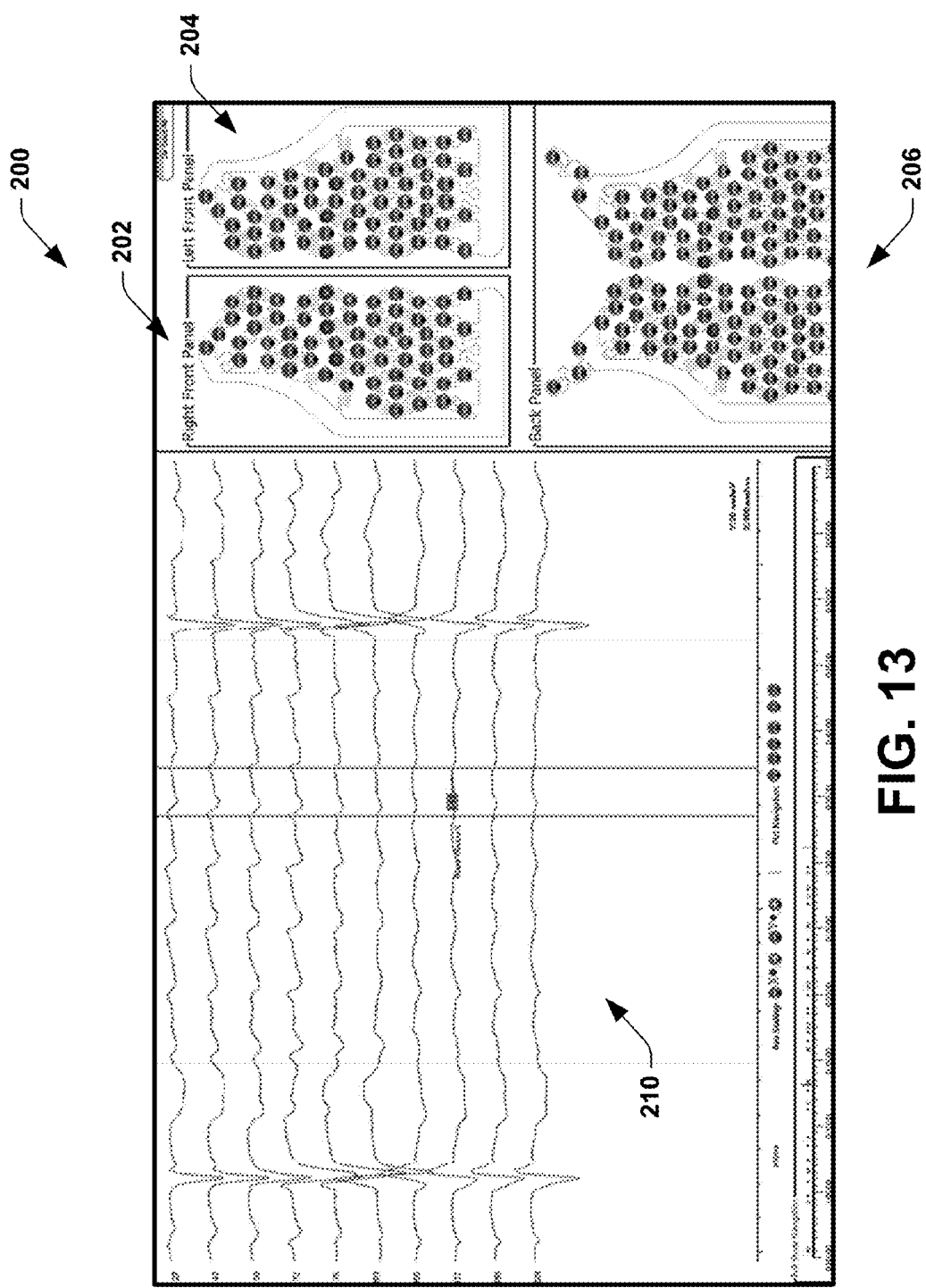
FIG. 13 depicts an example of screen shot of a display demonstrating a set of signals for corresponding electrode locations distributed across a patient's body.

FIG. 13 depicts an example of an interactive display, such as can be generated by the output generator 48 or mapping system 162. In the example of FIG. 13, the output corresponds to a plurality of signals that can be analyzed. For example, the signals can correspond to a selected set of signals distributed across the patient's body such as may be distributed across various portions of the patient's torso such as including a right portion panel 202, a left portion panel 204 and a back panel 206. The respective panels can correspond to an arrangement of electrodes having a particular distribution and which can cover the patient's torso with a generally even distribution of electrodes. In some examples, the electrodes can correspond to a vest or other configurations may also be used. The display 200 can be interactive in that a user can select one or more of the electrodes such as by selecting them from the respective panel graphical user interface elements 202, 204 and 206. In response, electrical signals for each selected electrode can be presented in the corresponding display window as demonstrated at 210. The display window can be utilized to identify durations of signals manually or automatically to identify F waves in each of the signals to enable analysis by the signal processor such as disclosed herein.

EXAMPLE APPLICATIONS

As mentioned, the systems and methods disclosed herein are applicable and relevant in patient screening, procedural planning, procedural workflow, post procedure evaluation, and follow-up. The following examples provide some examples of how such systems and methods can be used in various phases of clinical environment.

Example 1: Screening, Procedural Planning, Post-Procedural Evaluation

When triaging patients and screening them for different possible treatment options, one or more indicators of arrhythmogenicity disclosed herein can be determined for different electrode configurations as follows:
 a) For Multi-electrode array:
  i) The greater number of spatial zones that are identified by the signal processor as indicating stable arrhythmogenic activity tends to suggest that a patient has more arrhythmogenic substrate. In response, a health care provider may triage the patient towards drug therapy as opposed to an ablation, allowing more positive substrate modification prior to a future ablation.
  ii) Conversely, if a patient has fewer zones that are identified by the signal processor as indicating stable arrhythmogenic activity, such results can suggest a very specific set of regions are responsible for the arrhythmia, such that the patient could be considered a good candidate for ablation.
 b) For single electrode or 12-Lead ECG:
  i) The higher percentage of time a given patient exhibits stable driver trends (e.g., determined by trend analyzer 98), the more arrhythmogenic the substrate of his heart is. This information can be utilized by a health care provider to triage the patient towards drug therapy as opposed to an ablation, allowing more positive substrate modification prior to a future ablation.
  ii) Conversely, if a patient exhibits a lower percentage of time that the patient exhibits driver trends (e.g., determined by trend analyzer 98), the patient could be identified a good candidate for ablation.
2) Procedural Planning: When it is decided that a patient is a good candidate for ablation, systems and methods disclosed herein can be implemented for different electrode configurations to help plan a procedure as follows:
 a) Multi-electrode array:
  i) If a dense set of electrode nodes frequently indicate stable arrhythmogenic activity, such results can suggest that this patient has a primary driver and thus would be a good candidate for ablation.
  ii) Conversely if no single zone has been clearly indicated more than others, it could show that multiple drivers are sustaining the arrhythmia, and a more extensive ablation is required.
 b) Single electrode or 12-Lead ECG:
  i) The higher percentage of time a given patient exhibits stable driver trends (e.g., determined by trend analyzer 98), the more arrhythmogenic the substrate of his heart is. This information can further indicate that this patient will likely require a longer or more extensive ablation.
  ii) Conversely, if a patient exhibits a lower percentage of time that the patient exhibits driver trends, the results can indicate that this patient will require a shorter or less extensive ablation.
3) The following presents another example of a procedural workflow that can be implemented during a live ablation, in which systems and methods disclosed herein can provide indicators of arrhythmogenicity to be used in various electrode configurations.
 a) Multi-electrode array:
  i) A baseline recording could give the physician an initial understanding of how arrhythmogenic a patient is
  ii) During the ablation if the number of zones implicated, or how frequent zone is implicated, it could indicate positive, neutral, or negative effect. For example:
   (1) If the zones increase in number, or the frequency a node is implicated increases, this could indicate a negative effect from ablation, and the physician should stop ablating the zone they are currently targeting.
   (2) If the zones decrease in number, or the frequency a node is implicated decreases, this could indicate a positive effect from ablation and the physician should continue to target that zone or you have completed targeting an effective zone.
   (3) If the zones do not change, and the frequency a node is implicated does not change, this could indicate that there has been a neutral effect from ablation, and the physician is not targeting the correct zone.
 b) Single-electrode array:
  i) A baseline recording could give the physician an initial understanding of how arrhythmogenic a patient is.
  ii) During the ablation if the percentage of time a patient exhibits driver trends changes, it could indicate positive, neutral, or negative effect. For example:
   (1) If the percentage increases, this could indicate a negative effect from ablation, and the physician should stop ablating the zone they are currently targeting.
   (2) If the percentage decreases, this could indicate a positive effect from ablation and the physician should continue to target that zone or you have completed targeting an effective zone.
   (3) If percentage does not change, this could indicate that there has been a neutral effect from ablation, and the physician is not targeting the correct zone.
4) The following presents another example of a method that can be implemented using systems and methods disclosed herein as part of post-procedural evaluation. For example, prior to being discharged after an ablation, if the patient remains in their arrhythmia, systems and methods disclosed herein can be implemented for different electrode configurations to determine the presence or absence of stable arrhythmogenic activity.
 a) Multi-electrode array:
  i) If systems and methods disclosed herein frequently indicate a dense set of nodes, it could suggest that this patient has a primary driver and that was not adequately addressed during the acute ablation.
  ii) Conversely if no single zone has been clearly indicated more than others, it could show that multiple drivers are sustaining the arrhythmia, and could be a sign of the normal healing process acutely after an ablation.
   b) Single electrode or 12-Lead ECG:
      i) The higher percentage of time the patient exhibits driver trends, the more arrhythmogenic the substrate of his heart is. This could indicate to the physician that this patient had not been adequately ablated.
      ii) Conversely, if a patient exhibits a lower percentage of time that the patient exhibits driver trends, it could suggest less arrhythmogenic substrate, and it could indicate to the physician that this patient is in a normal recovery phase.
5) The following presents another example of a method that can be implemented using systems and methods disclosed herein as part of long-term follow-up. For example, during the chronic recovery phase, as defined as any time point past the patient being discharged from the hospital after invasive treatment (e.g., ablation), systems and methods disclosed herein can be used to evaluate patient condition.
   a) Multi-electrode array:
      i) If systems and methods disclosed herein frequently indicate a dense set of nodes exhibit stable arrhythmogenic activity, it could suggest that this patient has a primary driver and that was not adequately addressed during the acute ablation and could be a good candidate for re-ablation.
      ii) Conversely if no single zone has been clearly indicates stable arrhythmogenic activity more than others, this can suggest that multiple drivers are sustaining the arrhythmia, and could be a sign of the normal healing process acutely after an ablation treatment, or if a sufficient time has passed, that the patient requires drug therapy to enable positive substrate modification and is not a good candidate for re-ablation.
   b) Single electrode or 12-Lead ECG:
      i) The higher percentage of time the patient exhibits driver trends, the more arrhythmogenic the substrate of his heart is. This could indicate to the physician that this patient will require a longer or more extensive re-ablation.
   c) Conversely, if a patient exhibits a lower percentage of time that the patient exhibits driver trends, it could suggest less arrhythmogenic substrate, and it could indicate to the physician that this patient will require a shorter or less extensive re-ablation.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A system comprising:
   an input to receive at least one electrophysiological signal representing cardiac electrical activity measured from a body surface of a patient; and
   a signal processor, including at least two of a cycle length calculator, a signal amplitude calculator and a polarity calculator, to analyze the at least one signal and compute a score having a value to indicate a likelihood of arrhythmogenic activity, the score being computed as a function of at least two of cycle length, amplitude and polarity of the at least one signal as computed by the at least two calculators,
   wherein the at least one signal is known to map deterministically to a corresponding location on the patient's heart, such that the likelihood of arrhythmogenic activity derived from the computed signal characteristics provides an estimate of arrhythmogenic activity at the corresponding location on the patient's heart, and
   an output generator to generate an output corresponding to the likelihood of arrhythmogenic activity based on the score.

2. The system of claim 1, wherein the cycle length calculator is programmed to compute the cycle length for a plurality of cycles of the least one signal.

3. The system of claim 2, wherein the cycle length calculator computes the cycle length to characterize changes in the cycle length in a sequence of cycles that occur during at least one of a plurality of fibrillatory wave intervals of the at least one signal.

4. The system of claim 3, wherein the cycle length calculator identifies acceleration or deceleration of cardiac rhythm based on comparing temporal variations for the changes in the cycle length in the sequence of cycles during the at least one fibrillatory wave interval relative to a cycle length acceleration threshold.

5. The system of claim 1, wherein the signal amplitude calculator is programmed to compute changes in the amplitude of the least one signal during at least one of a plurality of fibrillatory wave intervals.

6. The system of claim 1, wherein the polarity calculator is programmed to compute changes in the polarity of the at least one signal during at least one of a plurality of fibrillatory wave intervals.

7. The system of claim 1, wherein the at least one signal comprises a plurality of signals acquired from a plurality of leads coupled to electrodes distributed at respective locations on the body surface.

8. The system of claim 7, wherein the signal processor computes values for each of the cycle length, the amplitude and the polarity of the at least one signal over at least one of a plurality of fibrillatory wave intervals identified in each of the plurality of signals such that each of the computed values specifies a temporal and/or spatial variability thereof.

9. The system of claim 7, wherein the signal processor comprises a phase calculator to compute an indication of phase characteristics for each of the plurality of signals during at least one fibrillatory wave interval thereof, the signal processor determining the likelihood of arrhythmogenic activity based on at least one of spatial and temporal variability in the phase characteristics.

10. The system of claim 1, further comprising a preprocessing block to receive the at least one electrophysiological signal, remove non-arrhythmogenic characteristics from the at least one signal and provide preprocessed data that is stored in memory, the signal processor computing the score based on the preprocessed data.

11. The system of claim 1, wherein the signal processor comprises frequency analyzer that analyzes predetermined frequency characteristics of the at least one signal during each of a plurality of fibrillatory wave intervals.

12. The system of claim 1, wherein the signal processor computes the score as a function of a change in the cycle length and at least one more of the amplitude or polarity for one or more fibrillatory wave of the at least one signal to indicate a likelihood of stable atrial fibrillation driver activity.

13. The system of claim 1, further comprising a therapy delivery system configured to control delivery of a therapy directly to a patient's heart based on the computed score.

14. The system of claim 1, wherein the at least one signal comprises a plurality of signals acquired from a plurality of leads coupled to electrodes distributed at respective locations on the body surface, the system further comprising:

a reconstruction engine programmed to compute reconstructed electrical signals on a cardiac envelope based on the plurality of signals and geometry data describing a spatial relationship between the electrodes and the patient anatomy including the body surface;

a driver calculator programmed to compute an indication of driver activity for the cardiac envelope based on the reconstructed electrical signals.

15. The system of claim 1, wherein the signal processor further comprises a fibrillatory wave detector that identifies at least one fibrillatory wave interval in the at least one electrophysiological signal, wherein the signal processor computes the score based on at least two of a change in cycle length for each fibrillatory wave, a change in amplitude of each fibrillatory wave and a polarity change for each fibrillatory wave of the at least one signal.

16. The system of claim 1, further comprising an input interface electrically connected to receive a plurality of electrophysiological signals representing cardiac electrical activity measured from the body surface of the patient, the signal processor analyzing each of the electrophysiological signals and computing the score to indicate a likelihood of arrhythmogenic activity for each of the electrophysiological signals.

17. The system of claim 16, further comprising a preprocessing hardware and software that removes non arrhythmogenic characteristics from each of the electrophysiological signals from the input interface and provides corresponding preprocessed data, the signal processor computing the score based on the preprocessed data.

18. The system of claim 1, wherein the output is presented on a display device.

19. One or more non-transitory machine-readable storage media having data and instructions executable by a processor to perform a method, the data including measurement data representing at least one electrophysiological cardiac signal measured via at least one electrode positioned a body surface of a patient, the method comprising:

analyzing the at least one electrophysiological signal to calculate at least two of cycle length, amplitude, and polarity of the at least one signal, and computing a score having a value to indicate a likelihood of arrhythmogenic activity, the score being computed as a function of the at least two of cycle length, amplitude and polarity of the at least one signal, wherein the at least one signal is known to map deterministically to a corresponding location on the patient's heart, such that the likelihood of arrhythmogenic activity derived from the computed signal characteristics provides an estimate of arrhythmogenic activity at the corresponding location on the patient's heart, and generating an output corresponding to the likelihood of arrhythmogenic activity based on the score.

* * * * *